United States Patent
Markovic et al.

(10) Patent No.: US 10,980,487 B2
(45) Date of Patent: Apr. 20, 2021

(54) SYSTEMS AND METHODS FOR REDUCING NOISE CAUSED BY STIMULATION ARTIFACTS IN NEURAL SIGNALS RECEIVED BY NEURO-MODULATION DEVICES

(71) Applicant: The Regents of the University of California, Oakland, CA (US)

(72) Inventors: Dejan Markovic, Los Angeles, CA (US); Ali H. Sayed, Oakland, CA (US); Sina Basir-Kazeruni, Los Angeles, CA (US); Stefan Vlaski, Karben (DE); Hawraa Salami, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 81 days.

(21) Appl. No.: 16/306,234

(22) PCT Filed: May 31, 2017

(86) PCT No.: PCT/US2017/035297
§ 371 (c)(1),
(2) Date: Nov. 30, 2018

(87) PCT Pub. No.: WO2017/210352
PCT Pub. Date: Dec. 7, 2017

(65) Prior Publication Data
US 2019/0125269 A1    May 2, 2019

Related U.S. Application Data

(60) Provisional application No. 62/343,777, filed on May 31, 2016.

(51) Int. Cl.
*A61N 5/00* (2006.01)
*A61B 5/00* (2006.01)
(Continued)

(52) U.S. Cl.
CPC .............. *A61B 5/7217* (2013.01); *A61B 5/00* (2013.01); *A61B 5/04* (2013.01); *A61B 5/04001* (2013.01);
(Continued)

(58) Field of Classification Search
CPC ........... A61B 5/7217; A61B 5/04; A61B 5/00; A61B 5/04001; A61B 5/7246;
(Continued)

(56) References Cited

U.S. PATENT DOCUMENTS

2006/0149337 A1*  7/2006  John .................. A61N 1/37235
                                                                607/45
2007/0118047 A1   5/2007  Tracey et al.
(Continued)

FOREIGN PATENT DOCUMENTS

CN    109310329 A    2/2019
EP    3463060 A1     4/2019
(Continued)

OTHER PUBLICATIONS

Extended European Search Report for European Application 17807433.2, Report Completed Nov. 22, 2019, dated Dec. 2, 2019, 10 Pgs.
(Continued)

*Primary Examiner* — Rex R Holmes
(74) *Attorney, Agent, or Firm* — KPPB LLP

(57) ABSTRACT

System and methods that cancel artifacts of stimulation signals from neural signals are disclosed. In several embodiments, the systems and methods determine a threshold value for the neural signal in the absence of artifacts. The threshold value can then be used to detect an artifact in received neural signals. In a number of embodiments, a template can be used to cancel an artifact from a neural signal in response to the neural signal being greater than the threshold value.

19 Claims, 16 Drawing Sheets

(51) Int. Cl.
    *A61N 1/18*     (2006.01)
    *A61B 5/04*     (2006.01)
    *A61N 1/36*     (2006.01)
    *A61N 1/08*     (2006.01)
    *A61N 1/00*     (2006.01)
    *A61N 1/05*     (2006.01)

(52) U.S. Cl.
    CPC ................ *A61N 1/00* (2013.01); *A61N 1/05* (2013.01); *A61N 1/0551* (2013.01); *A61N 1/08* (2013.01); *A61N 1/18* (2013.01); *A61N 1/36* (2013.01); *A61N 1/36125* (2013.01); *A61B 5/725* (2013.01); *A61B 5/7246* (2013.01)

(58) Field of Classification Search
    CPC ..... A61B 5/725; A61B 5/0476; A61B 5/7203; A61N 1/18; A61N 1/36; A61N 1/08; A61N 1/00; A61N 1/05; A61N 1/0551; A61N 1/36125
    See application file for complete search history.

(56) References Cited

U.S. PATENT DOCUMENTS

| | | |
|---|---|---|
| 2008/0183088 A1 | 7/2008 | Lian et al. |
| 2009/0125081 A1 | 5/2009 | Spitzer et al. |
| 2010/0068751 A1 | 3/2010 | Eberle |

FOREIGN PATENT DOCUMENTS

| | | |
|---|---|---|
| JP | 2019522511 A | 8/2019 |
| WO | 2015191628 A1 | 12/2015 |
| WO | 2017210352 A1 | 12/2017 |

OTHER PUBLICATIONS

International Preliminary Report on Patentability for International Application PCT/US2017/035297, Report dated Dec. 4, 2018, dated Dec. 13, 2018, 6 Pgs.

International Search Report and Written Opinion for International Application No. PCT/US2017/035297, Search completed Jul. 17 2017, dated Aug. 4, 2017, 7 Pgs.

Basir-Kazeruni et al., "A Blind Adaptive Stimulation Artifact Rejection (ASAR) Engine for Closed-Loop Implantable Neuromodulation Systems", Proceedings of the 8th International IEEE/EMBS Conference on Neural Engineering (NER), Shanghai, China, May 25-28, 2017, pp. 186-189.

Blum et al., "Models of stimulation artifacts applied to integrated circuit design", The 26th Annual International Conference of the IEEE Engineering in Medicine and Biology Society, Sep. 1-5, 2004, vol. 2, San Francisco, CA, USA, pp. 4075-4078, DOI: 10.1109/IEMBS.2004.1404137.

Brown et al., "Stimulus-Artifact Elimination in a Multi-Electrode System", IEEE Transactions on Biomedical Circuits and Systems, Mar. 2008, vol. 2, No. 1, pp. 10-21, DOI: 10.1109/TBCAS.2008.918285.

Erickson et al., "Iterative Covariance-Based Removal of Time-Synchronous Artifacts: Application to Gastrointestinal Electrical Recordings", IEEE Transactions on Biomedical Engineering, 2016, vol. 63, No. 11, pp. 2262-2272.

Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.

Mendrela et al., "A Bidirectional Neural Interface Circuit With Active Stimulation Artifact Cancellation and Cross-Channel Common-Mode Noise Suppression", IEEE Journal of Solid-State Circuits, Apr. 2016, Date of Publication: Jan. 1, 2016, vol. 51, No. 4, pp. 955-965, DOI: 10.1109/JSSC.2015.2506651.

Mendrela et al., "Enabling Closed-Loop Neural Interface: A Bi-Directional Interface Circuit With Stimulation Artifact Cancellation and Cross-Channel CM Noise Suppression", 2015 Symposium on VLSI Circuits (VLSI Circuits), Jun. 17-19, 2015, Kyoto, Japan, pp. C108-C109, DOI: 10.1109/VLSIC.2015.7231342.

Wagenaar et al., "Real-Time Multi-channel Stimulus Artifact Suppression by Local Curve Fitting", Journal of Neuroscience Methods, Oct. 30, 2002, vol. 120, No. 2, pp. 113-120, https://doi.org/10.1016/S0165-0270(02)00149-8.

Zhang et al., "Intraoperative Neurological Monitoring: Continuous Evoked Potential Signal Extraction and Analysis", IEEE Transactions on Biomedical Engineering, 2006, pp. 39-45.

Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.

\* cited by examiner

SYSTEMS AND METHODS FOR REDUCING NOISE CAUSED BY STIMULATION ARTIFACTS IN NEURAL SIGNALS RECEIVED BY NEURO-MODULATION DEVICES

CROSS REFERENCED APPLICATIONS

This Application is a national stage of PCT Patent Application No. PCT/US2017/035297, entitled "Systems and Methods for Reducing Noise Caused By Stimulation Artifacts in Neural Signals Received By Neuro-Modulation Devices" to Markovic et al., filed May 31, 2017, which claims priority to U.S. Provisional Patent Application No. 62/343,777, entitled "System And Method for Reducing Noise Caused by Stimulation Artifacts in Neural Signals Received By a Neuro-Modulation Device" file May 31, 2016 that is hereby incorporated by reference as if set forth herewith.

STATEMENT FOR FEDERAL SUPPORT

This invention was made with government support under grant number DARPA-BAA-14-08 and N66001-14-2-4029, awarded by the U.S. Department of Defense, Defense Advanced Research Projects Agency, Microsystems Technology Office. The government has certain rights in the invention.

FIELD OF THE INVENTION

This invention relates to a neuro-modulation device. More particularly, this invention relates to reduction of noise in neural signals received by neuro-modulation devices. Still more particularly, this invention relates to reducing noise introduced into the neural signals from simulation signals.

BACKGROUND

Neuro-modulation devices are used to measure neural signals in many medical procedures. Often these procedures apply a stimulation signal and use the neuro-modulation device to measure and record neural signals that are generated in response to the stimulation signal. The presence of stimulation signal artifacts observed by a neuro-modulation device can be a problem in realizing concurrent stimulation and recording of neural signals. In particular, given that the frequency content of these artifacts is within the required signal bandwidth of the received neural signals, a simple frequency-selective filtering technique typically cannot be used to attenuate the artifacts. Existing solutions (e.g., blanking the recording channel during stimulation, self-cancelling stimulation electrodes, etc.) have not overcome all the challenges faced in reducing the noise from these artifacts. Furthermore, the existing solutions lack the ability to perform continuous neural signal recording during the stimulation phase rendering a critical portion of the data unusable.

SUMMARY

An advance in the art is made by systems and methods for reducing noise caused by stimulation artifacts in neural signals received by neural modulation devices in in accordance with some embodiments of this invention. A process from cancelling stimulation artifacts from neural signals in accordance with some embodiments of the invention is performed in the following manner. Neural signals are received from a first sensor. The received neural signals are in the absence of stimulation artifacts. Statistics for the neural signals received from the first sensor are determined from the received neural signals. A threshold value for neural signals is set based on the statistics for neural signals received from the first sensor. A template of stimulation artifacts is determined based on the threshold value. An adaptive filter is configured based upon the template. Neural signals from a second sensor are then received and stimulation artifacts are removed from the neural signals of the second sensor using the adaptive filter configured using the template to obtain clean neural signals.

In accordance with many embodiments, the neural signals from the first sensor are obtained by sampling the neural signal from the first sensor to obtain the first N sample of the neural signal. N may chosen as $N=2^n$ for some n and the processing system performs multiply and divide operations using binary shift operations in accordance with a number of these embodiments.

In accordance with some embodiments, the determined statistics for neural signals received from the first sensor include a mean of the neural signals and a standard deviation of the neural signals. The wherein statistics for neural signals received from the first sensor may be determined in the following manner in accordance with a number of embodiments. The values $S_{(i)}$ and $T_{(i)}$ may be recursively updated in accordance with the following equations $S_{(i)}=S_{(i-1)}+x_{(i)}$ and $T_{(i)}=T_{(i-1)}+x^2_{(i)}$, where $x_{(i)}$ is the sample of the neural at time i. The mean for the neural signals may then be determined based on the following expression:

$$avg = \frac{S(N)}{N};$$

and the standard deviation of the neural signal is determined based on the following expression:

$$std \approx \sqrt{\frac{1}{N-1}(T(N) - N\ avg^2)}.$$

In accordance with some embodiments, the template is represented as $u_i \in R^{1 \times 16}$ and the determining of the template includes determining $u_i(\ell)$, the $\ell$-th element of the template, $u_i$, from the measurement of the neural signal at time i, $d_k(i)$, based on the following:

$$u_i = \begin{cases} d_k, (i-\ell), & \text{if } |d_k, (i-\ell) - avg| \geq \alpha \cdot std, \\ 0, & \text{otherwise} \end{cases}.$$

In accordance with some embodiments, a clean neural signal, $\hat{s}_k(i)$, is obtained by subtracting the estimated artifact $u_i w_{k,i}$ from $d_k(i)$ as follows:

$$w_{k,i} = w_{k,i-1} + \frac{\mu}{\|u_i\|^2 + \epsilon} u_i^T [d_k(i) - u_i w_{k,i-1}]$$

$$\hat{s}_k(i) = d_k(i) - u_i w_{k,i}$$

where $w_{k,i}$ is a filter coefficient.

In accordance with a number of embodiments, the adaptive filter is a Normalized Least Mean Square (NLMS) adaptive filter. In accordance with some of these embodiments, the NLMS adaptive filter is a 16-tap NLMS adaptive filter.

DETAILED DESCRIPTION

Turning now to the drawings, an energy-efficient implementation of an Adaptive Stimulation Artifact Rejection (ASAR) process capable of adaptively removing artifacts of stimulation signals from neural signals for varying stimulation characteristics at multiple sites in accordance with some embodiments of this invention are disclosed. In accordance with several embodiments, a blind artifact template detection technique is utilized, which in combination with the ASAR process can eliminate the need for any prior knowledge of the temporal and structural characteristics of the stimulation pulse. Furthermore, processes in accordance with some embodiments of the invention also effectively battle the non-linear mapping of brain tissue and non-idealities of electrode interfaces with linear filtering. In accordance with many embodiments, the use of a blind artifact template makes the ASAR process robust against uncertainties, misalignment, and/or asynchrony between the assumed stimulation characteristics and the actual stimulation applied to the system resulting from non-idealities of the timing, stimulator circuits, and/or sensing circuits that cause practical difficulties and/or errors in traditional architectures.

While a given ASAR process is typically motivated by the task and intrinsic difficulties of artifact removal in deep brain stimulation, ASAR processes in accordance with a number of embodiments of the invention are applicable to a wider range of problems including, but not limited to, non-linear mapping from artifact source to measurement; inaccurate or limited knowledge about the nature of the artifact; and/or constraints on acceptable processing power.

Previously Purposed Solutions

Others have proposed several other systems for cancelling artifacts from neural signals received from a neuro-modulation device. However, each of these proposed systems have some drawbacks the following are examples of a few of the proposed systems and the drawbacks associated with each system.

Overload Systems

One class of proposed system tries to mitigate stimulation signal artifacts by "blanking" the recording channel during or immediately after stimulation. The purpose of this "blanking" is to reduce the burden on analog front-ends that cannot support very high dynamic ranges necessary to capture neural signals alongside stimulation artifacts. An example of such a system is described in the paper entitled "Stimulus-Artifact Elimination in a Multi-Electrode System," Biomedical Circuits and Systems, IEEE Transactions on, vol. 2, no. 1, pp. 10, 21, March 2008 by Brown, E. A.; Ross, J. D.; Blum, R. A.; Yoonkey Nam; Wheeler, B. C.; DeWeerth, S. P. An overload recovery technique as described in this paper is shown in FIG. 1.

Figure 1:
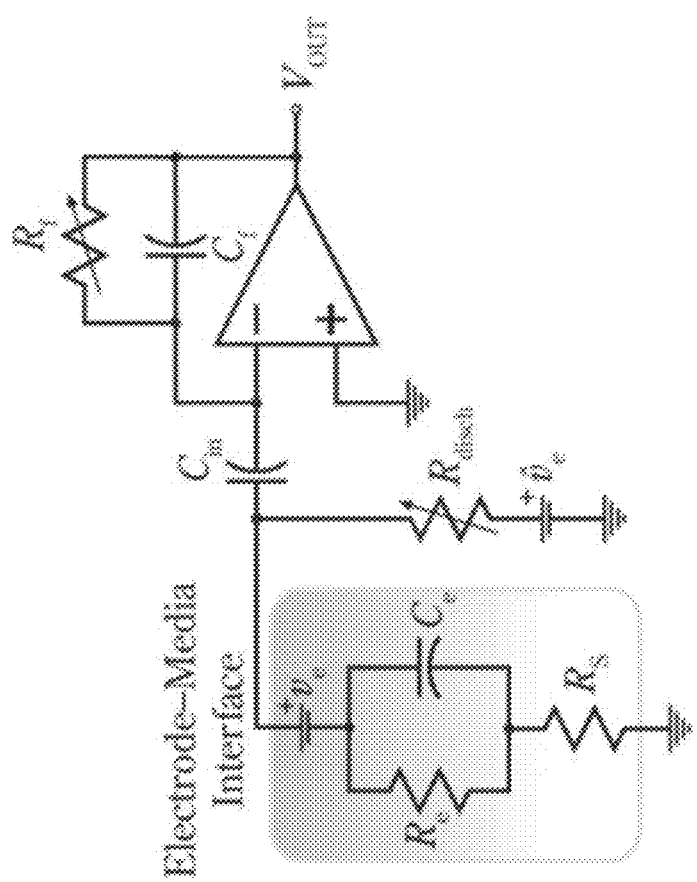
FIG. 1 illustrates circuitry used in an overload recovery technique involving cancelling artifact signals from received neural signals in accordance with the prior art.

In the system shown in FIG. 1, a shunt resistance is used to de-polarize an electrode, immediately after stimulation ends. In this example and most other cases, a quick recovery from saturation is achieved. However, it is clear that the capability to record neural signals during stimulation onset is not provided and a critical portion of neural signal recordings is rendered unusable.

Polynomial Curve Fit

Figure 2:
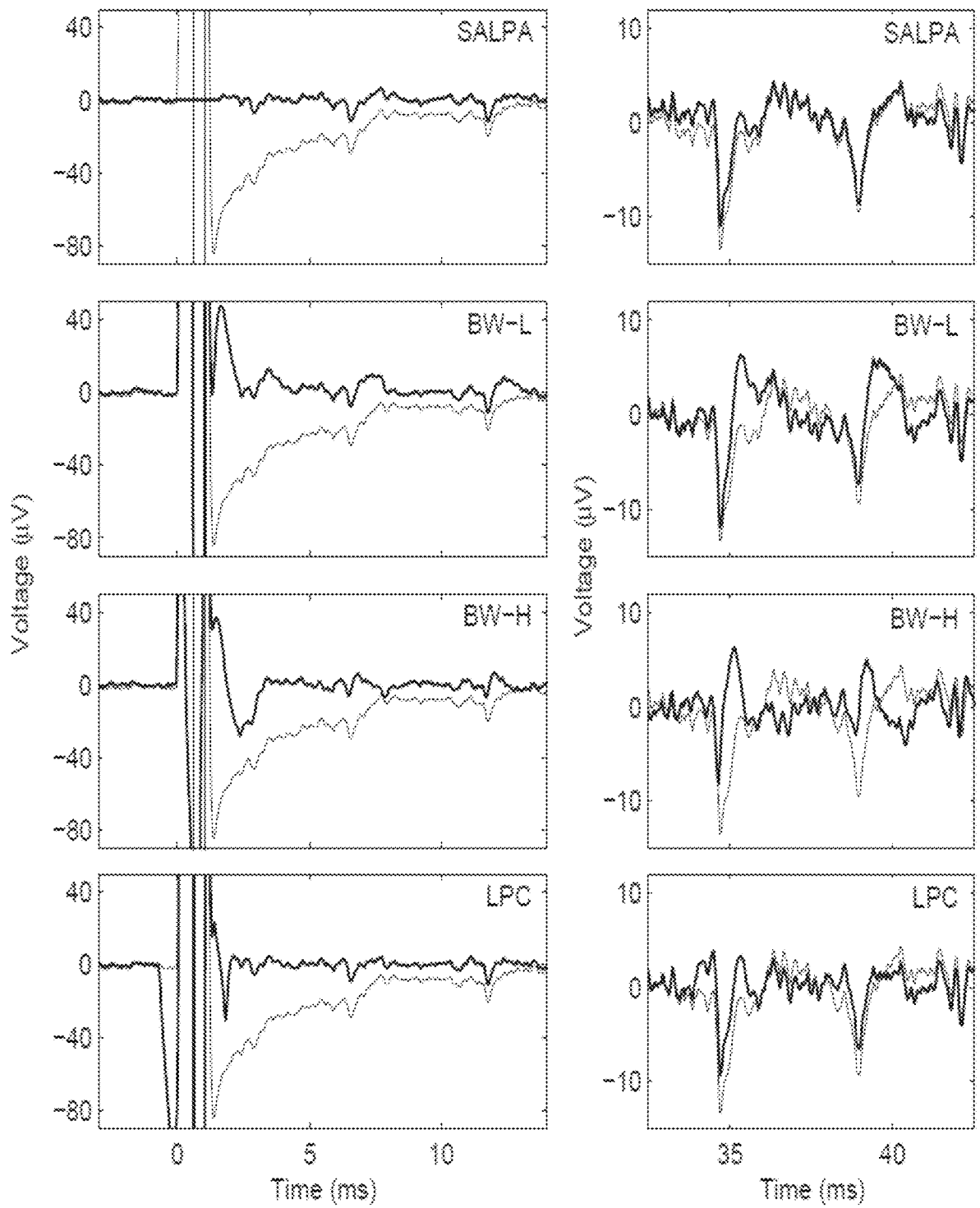
FIG. 2 illustrates graphs of signals that result from using a prior art curve fitting technique to remove artifact signals from received neural signals.
Figure 3:
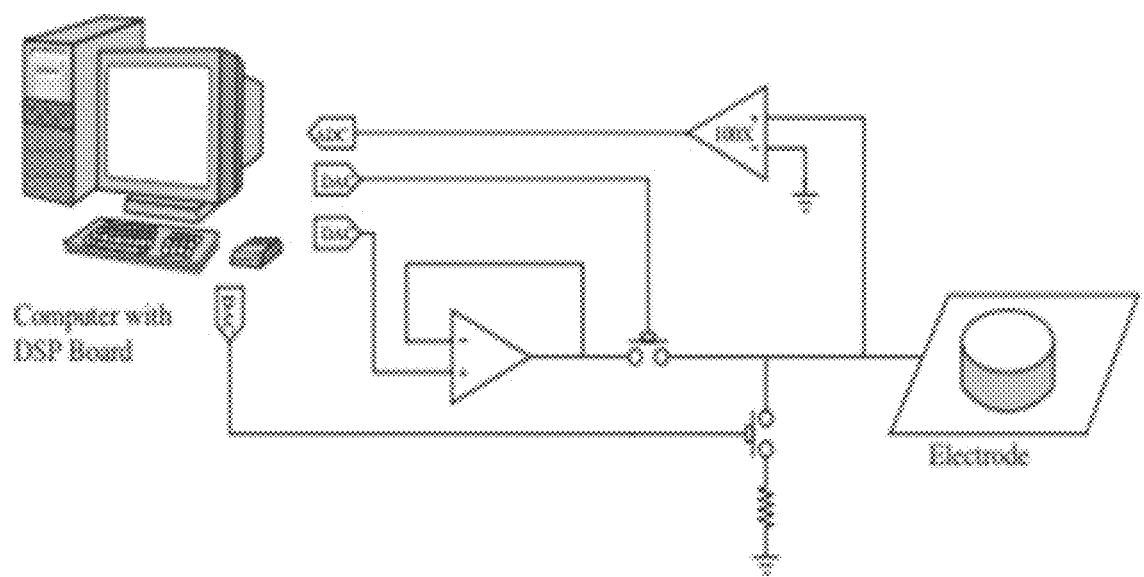
FIG. 3 illustrates a top level summary of a prior art technique for cancelling artifacts of simulation signals from received neural signals using artifact templates.

Another approach described in the paper entitled "Real-Time Multi-channel Stimulus Artifact Suppression by Local Curve Fitting," Journal of Neuroscience Methods, vol. 120, no. 2, pp. 113-120, 30 Oct. 2002 by D. A. Wagenaar, S. M. Potter is a local curve fitting technique. This approach is an algorithm implemented by a processing system receiving the neural signal and is called SALPA. The results of the SALPA technique using various curve-fitting methods are shown in FIG. 2. The SALPA technique blanks out the output of the recorded neural signals during stimulation. Although the performance of SALPA is significantly better than low-pass Butterworth (BW-L), high-pass Butterworth (BW-H), and linear phase filters, the performance of SALPA is still not satisfactory. Furthermore, the limited degree of freedom to model the artifact can hinder the applicability of SALPA. Most importantly, SALPA is an offline algorithm. Meaning that a bulk of data needs to be acquired before any portion of the data can be cleaned. This constraint typically renders systems using SALPA inapplicable to a majority of applications where (a) memory is limited, (b) computational power is limited, and/or (c) the cleaned data needs to be available in real-time.

Self-Cancelling Stimulation Electrode Configuration

Figure 4:
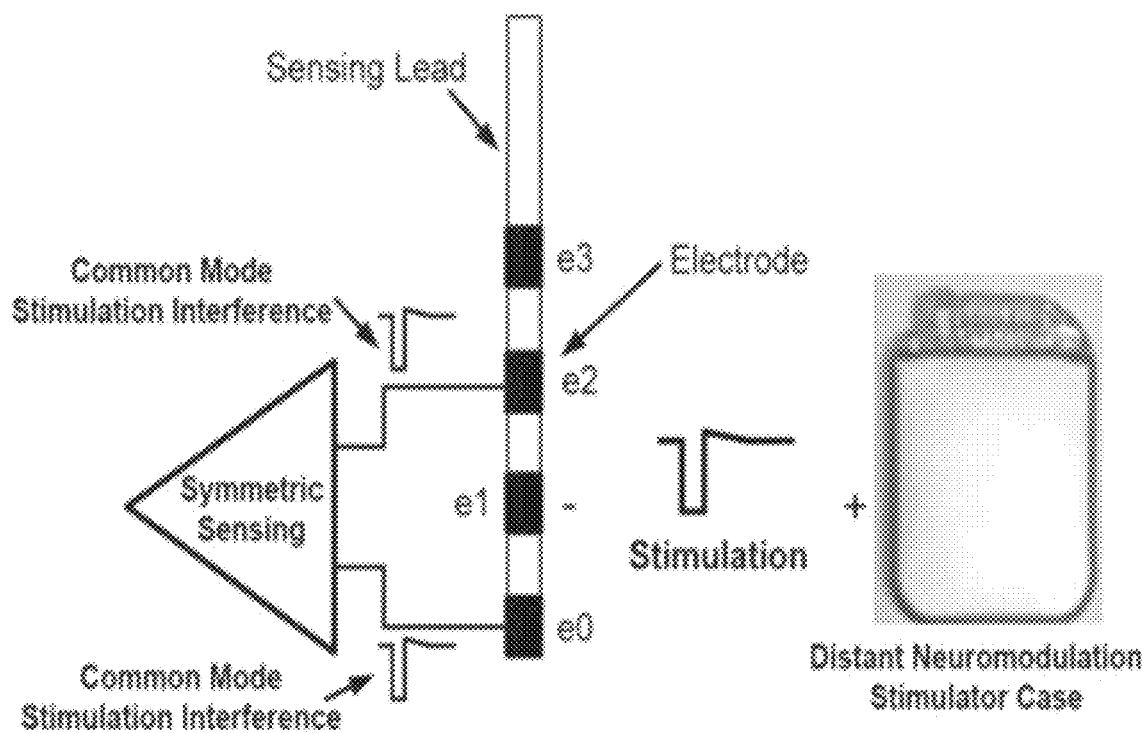
FIG. 4 illustrates a diagram of a system that uses self-cancelling stimulation electrodes for cancelling artifacts of simulation signals from received neural signals in accordance with an embodiment of the invention.

Another approach described in the paper entitled "Design and Validation of a Fully Implantable, Chronic, Closed-Loop Neuromodulation Device With Concurrent Sensing and Stimulation," Neural Systems and Rehabilitation Engineering, IEEE Transactions on, vol. 20, no. 4, pp. 410, 421, July 2012 by Stanslaski, Scott; et. al. is a self-cancelling stimulation electrode configuration. An illustration of the operation of a self-cancelling stimulation electrode configuration is shown in FIG. 4. In these types of systems, recording electrodes are placed differentially around stimulation electrodes and common-mode passive filters are utilized to attenuate the stimulation signal artifacts. It is a problem that this solution is very application-specific. Thus, unless a system is produced with a set configuration, the system cannot be effectively evaluated. Furthermore, electrode configuration requirements limit the flexibility that is offered to the user, as far as stimulation and recording sites are concerned. Another noteworthy observation in this work is that off-chip components are required which is undesirable. Additionally, the artifacts reside in frequency ranges that did not overlap the neural signals of interest for this system to be effective, which is not the case in many practical situations.

Echo-Cancellation Systems

Several systems that use echo-cancellation to cancel artifacts of the stimulation signals from received neural signals have been purposed in articles including Gnadt et al., "Spectral cancellation of microstimulation artifact for simultaneous neural recording in situ," Biomedical Engineering, IEEE Transactions on, vol. 50, no. 10, pp. 1129, 1135, October 2003; Adam E. Mendrela, et. al., "Enabling Closed-Loop Neural Interface: A Bi-Directional Interface Circuit with Stimulation Artifact Cancellation and Cross-Channel CM Noise Suppression," Proc. IEEE Symp. VLSI Circuits, June 2015; and Mendrela et al., "A Bidirectional Neural Interface Circuit With Active Stimulation Artifact Cancellation and Cross-Channel Common-Mode Noise Suppression," in IEEE Journal of Solid-State Circuits, no. 99, pp. 1-11. Echo-cancellation systems have shown great promise in concept. However, the performance of echo-cancellation systems is not nearly sufficient to be implemented in an implantable, real-time, closed-loop neuromodulation system.

Figure 5:
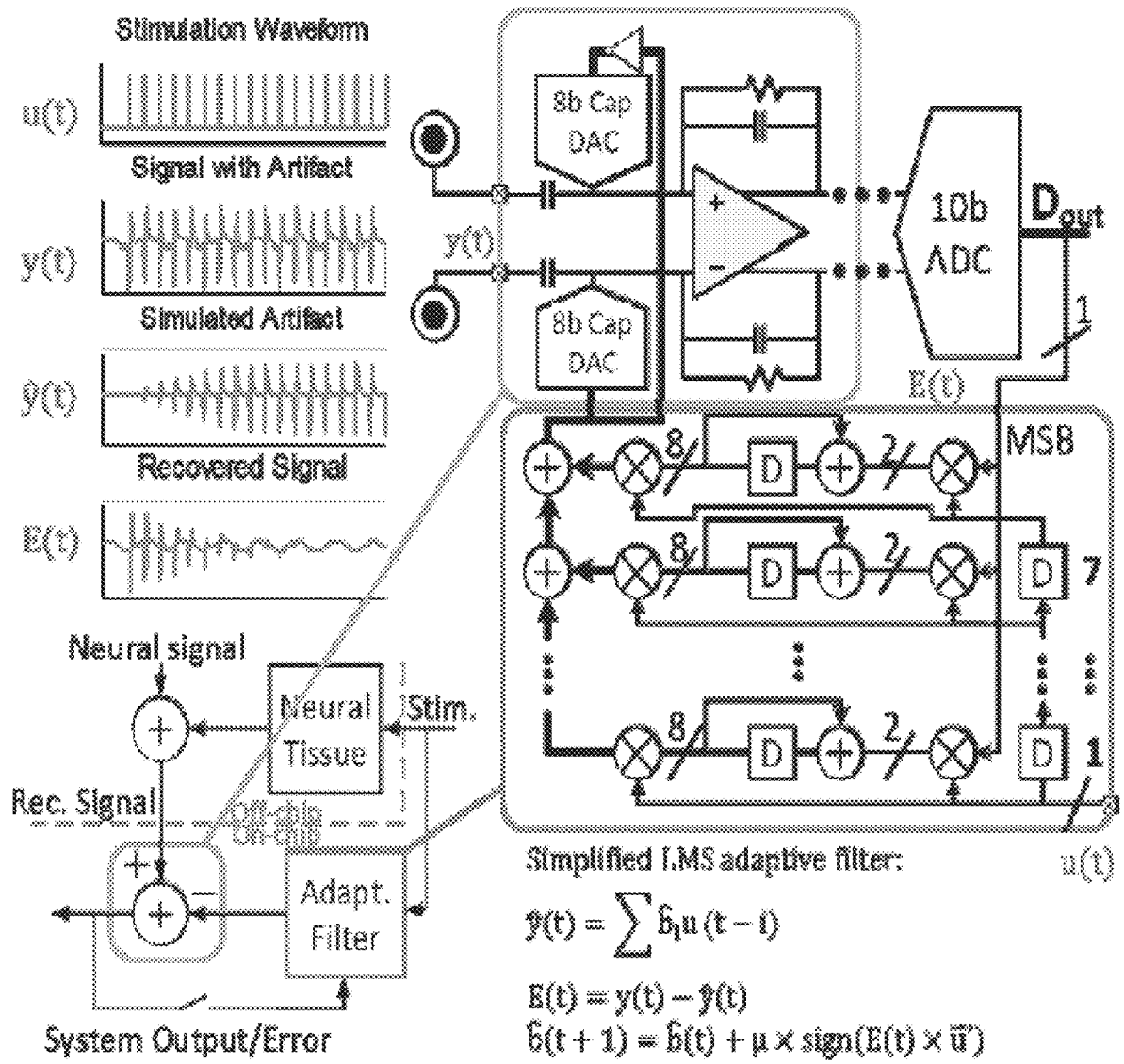
FIG. 5 illustrates a diagram of a system that uses an echo cancellation technique for cancelling artifacts of simulation signals from received neural signal in accordance with an embodiment of the invention.

An example of an echo-cancellation system is shown in FIG. 5. The shown echo-cancellation system performs the cancellation of estimated artifacts at the input of the amplifier, using a DAC, hence introducing the same input noise issues that were previously discussed in artifact cancellation systems. Additionally, echo-cancellation systems typically demonstrate very long convergence times (~3 seconds up to ~12 seconds), which is not practical in real life situations, where stimulation/recording sites along with stimulation pulse's structural and temporal characteristics can change at any moment. The feedback nature of artifact subtraction dictates a maximum delay between stimulation onset and when the cancellation is seen at the sensing end. If the delay is any longer, the method could fail, unless stimulation is periodic.

Adaptive Stimulation Artifact Rejection (ASAR) Systems

Figure 6:
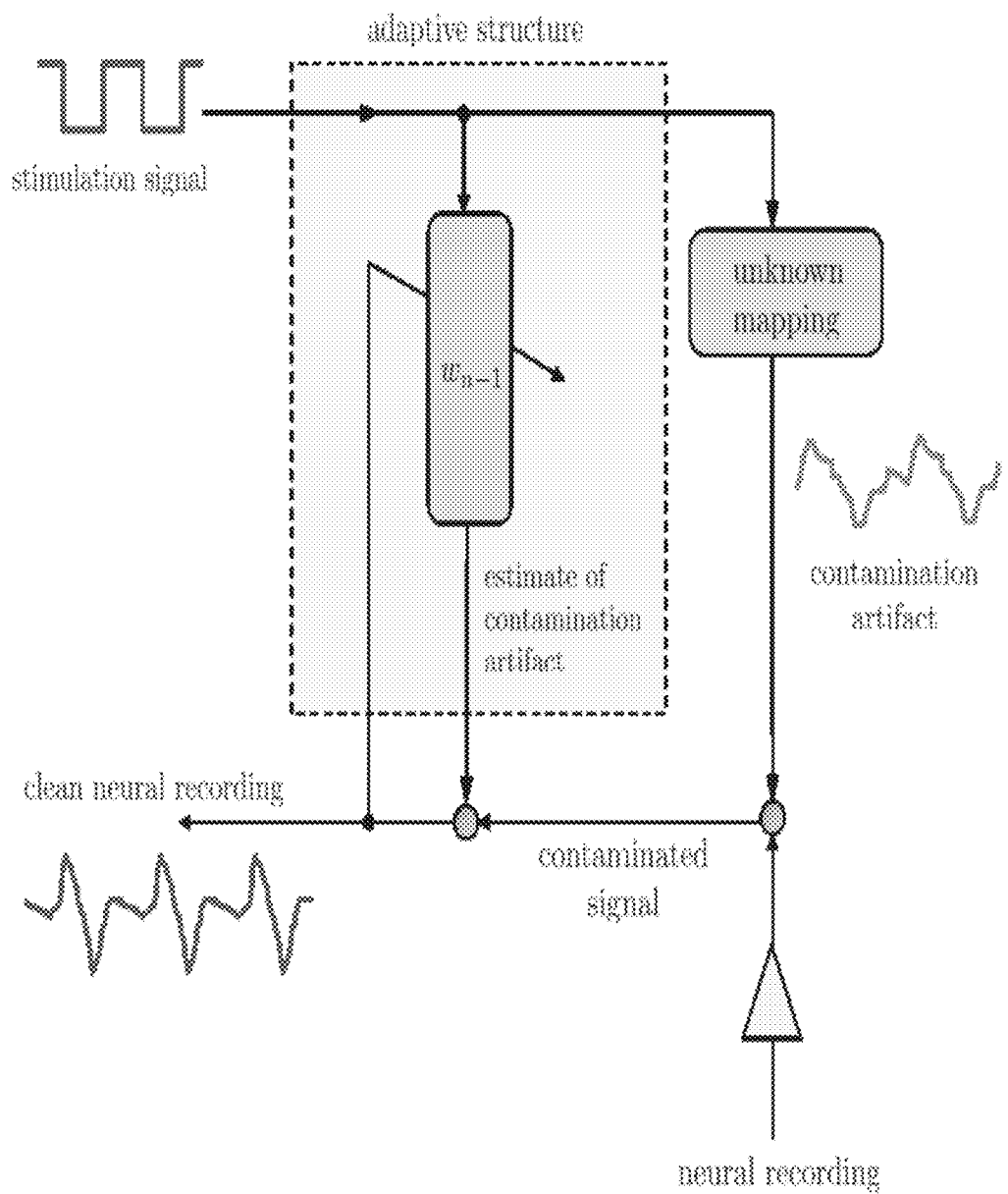
FIG. 6 illustrates a diagram of a system that uses an adaptive filtering technique for cancelling artifacts of simulation signals from received neural signals in accordance with an embodiment of the invention.

In accordance with some embodiments of this invention, a system that embeds the findings from echo-cancellation and other methods mentioned above into a comprehensive adaptive filtering framework and aims to provide a complete Adaptive Stimulation Artifact Rejection solution for modern low power, closed-loop neuromodulation systems is provided. The implementation of energy-efficient ASAR processes in accordance with several embodiments of the invention aims to clean neural recordings in the presence of stimulation artifact by utilizing adaptive filtering techniques. The motivation for an ASAR system in accordance with some embodiments of the invention is shown in FIG. 6. As can be seen in FIG. 6, an artifact with an unknown mapping is introduced into recorded neural signals by a stimulation signal. An ASAR process in accordance with some embodiments of the invention uses a filter structure uses an estimate of the contamination artifact to filter out the contamination artifact in the recorded neural signal to provide a clean signal.

Figure 7:
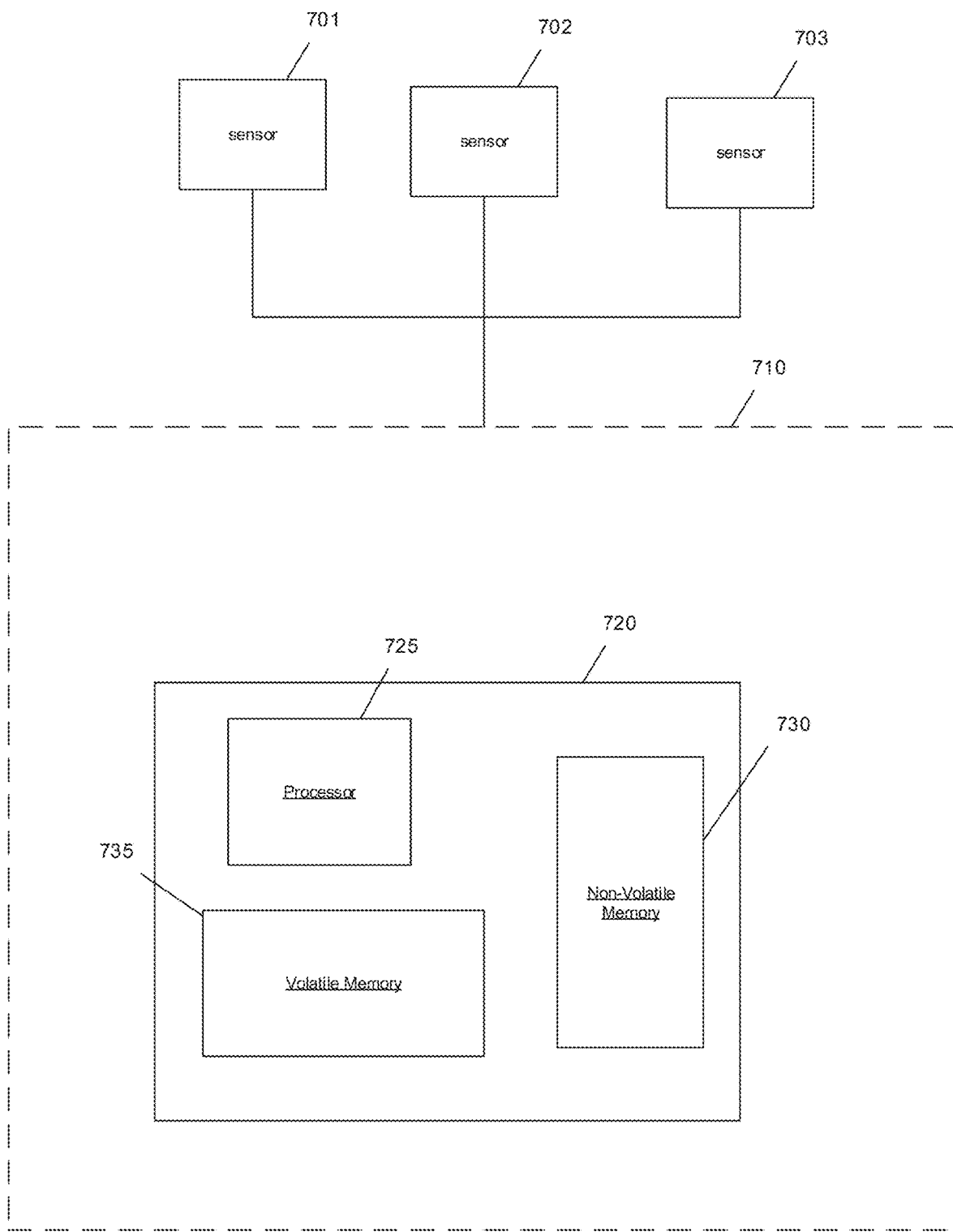
FIG. 7 illustrates a block diagram of a processing system in accordance with an embodiment of the invention.

A system that uses an ASAR process in accordance with an embodiment of the invention is shown in FIG. 7. Neuromodulation device 710 includes sensors 701-703 that are placed in close proximity to one another to detect and/or read neural signals generated in response to a simulation signal. Each sensor 701-703 transmits the read neural signals to neuro-modulation device 710. A processing system 720 in the neuro-modulation device receives the signals and performs the filtering to clarify and/or improve the read neural signals. Although not shown, neuro-modulation devices may include an interface system that transforms the read signals received from the sensors 701-703 into digital signals for processing system 720. Furthermore, in accordance with some embodiments, the processing system 720 is separate from the neural-modulation devices and receives the read signals from the neural modulation device via a connection that may be either wireless or hard-wired. In accordance with some other embodiments, the neuro modulation device may be implemented by or incorporated into the processing device.

In FIG. 7, processing system 720 includes a processor 725, a non-volatile memory 730, and a volatile memory 735. The processor 725 is a processor, microprocessor, controller, or a combination of processors, microprocessor, and/or controllers that performs instructions stored in the volatile 735 and/or the non-volatile memory 730 to manipulate data stored in the memory. The non-volatile memory 730 can store the processor instructions utilized to configure the processing system 720 to perform processes including processes in accordance with various embodiments of the invention and/or data for the processes being utilized. In other embodiments, the processing system software and/or firmware can be stored in any of a variety of non-transient computer readable media appropriate to a specific application. In the illustrated embodiment, the network interface is a device that allows processing system 720 to transmit and receive data over a network based upon the instructions performed by processor 725. Although a processing system 700 is illustrated in FIG. 7, any of a variety of processing systems can be configured to provide methods and systems in accordance with certain embodiments of the invention.

Blind ASAR System

Figure 8:
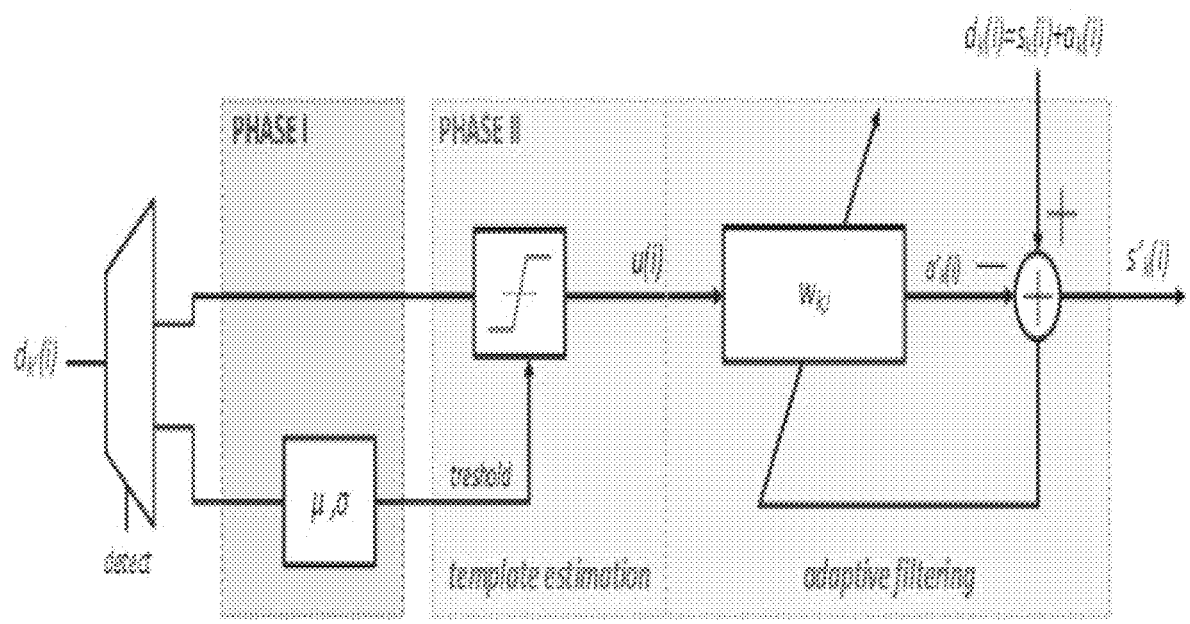
FIG. 8 illustrates a diagram of an algorithm for performing an adaptive filtering technique to cancel artifacts of simulation signals from received neural signals in accordance with an embodiment of the invention.

A system that cancels artifacts of stimulation signals from received neural signals using ASAR in accordance with an embodiment of the invention is shown in FIG. 8. In accordance with this embodiment, K measurement sites are distributed spatially. At each particular electrode, k, and time instance, i, the artifact is modeled as:

$$a_k = u_{k,i} w_k$$

Where $u_{(k,i)}$ and $w_k$ are vectors of size M. Note that this representation assumes that the artifact is generated as a linear transformation from $u_{(k,i)}$ to $w_k$. The most straightforward approach would be to populate $u_{(k,I)}$ from the stimulation pattern. This has several major drawbacks, namely that: (a) the stimulation needs to be known; (b) the algorithm can only cancel linear transformations of the stimulation pattern, which is typically not sufficient in practice; and (c) the method is highly susceptible to errors stemming from non-idealities, asynchrony and/or misalignment. In accordance with some embodiments of the invention, $u_{(k,I)}$ is directly obtained from measured data and used to cancel artifacts in real-time without any prior knowledge about the nature of the stimulation. Furthermore, the proposed algorithm absorbs the non-linearity correction implicitly into the computationally inexpensive generation of $u_{(k,I)}$ effectively allowing non-linear artifact rejection to be performed at approximately the cost of a linear adaptive filter.

In accordance with many embodiments, some electrodes are clustered in close spatial proximity to one another in order to allow for the incorporation of this information into the calculation of the weight vector. The ASAR process allows for the incorporation of multiple measurements by approximately solving for the weight vector $w_k$ as:

$$w_{N_k}^o = \mathrm{argmin}_w \Sigma_{l \in N_k} E \| d_l(i) - u_{l,i} w \|^2$$

Where $N_k$ is the set of electrodes in close proximity to electrode, k. The assumption in accordance with some of these embodiments is that $w_k \approx w_l$ for k in $N_k$. In accordance with some of these embodiments, ASAR allows, but does not require, multiple measurements to be utilized. The case where only measurements from electrode k are used to clean electrode k is admissible as a special case. In this case, the above sum collapses to a single element. In practice, electrode geometry and computational restrictions determine whether one or multiple measurements are utilized. In either case, the evaluation of the above expression is infeasible. Instead, the estimated weight vector $w_{N_k}^o$ is iteratively calculated and implemented in hardware in the following manner:

$$w_{N_k,i} = w_{N_k,i-1} + u' u_i^T \left[ \left( \sum_{l \in N_k} d_l(i) \right) - \mathrm{card}(N_k) u_i w_{N_k,i-1} \right]$$

$$\hat{s}_k(i) = d_k(i) - u_i w_{N_k,i}$$

Where, i is the time index, k is the electrode index (channel), w represents filter coefficients, u is a signal correlated with the artifact (can be the stimulation pulse or some approximate estimate of it), d is the measured signal, and ŝ is the cleaned neural signal.

In prior implementations of LMS adaptive filtering solutions for stimulation artifact rejection in neuro-modulation applications, a fixed step-size (μ') is used for calculation of error signals and the filter coefficients (w). The fixed step size is one of the reasons that the echo-cancellation and others methods typically suffer from very long convergence times and/or low accuracy. On the other hand, an ASAR system in accordance with some embodiments of the invention calculates an appropriate step-size each time a new sample is received (using norm calculations), and avoids dealing with accuracy vs convergence time trade-off resulting in comparatively faster convergence times.

Furthermore, a stimulation pulse can be used as the template for the adaptive filter in accordance with some embodiments of the invention. However, the use of a stimulation pulse as the template has several issues including but not limited to: (1) many non-idealities exist in the electrode interfaces; (2) unknown tissue mapping certainly changes the pulse shape seen at the recording site; (3) prior knowledge about the structural and temporal shape of the stimulation pulse is required; (4) adaptive filters typically require a longer convergence time to converge from a perfect stimulation pulse shape to one that would effectively remove stimulation artifacts at multiple recording sites; and (5) the filter is unable to resolve non-linear mappings.

To overcome these issues, systems in accordance with many embodiments of the invention use a blind template estimation method that eliminates any need for prior knowledge of structural and temporal characteristics of the stimulation pulse. The use of a blind template enables an assumption that no characteristics for stimulation need be known and sets no limits for delays between when a stimulation pulse is observed at various recording sites close or far. Most importantly, the blind template enables an ASAR system implementation to work with any arbitrary stimulation pulse. This is the main reason why a linear LMS adaptive filter in accordance with some embodiments of the invention can so effectively estimate and resolve a non-linear mapping (of the brain tissue). This enables a system in accordance with various embodiments of the invention to offer an innovative solution at a much lower computational complexity/cost. Lastly, a major difference is that the hardware implementations of ASAR processes in accordance with many embodiments of the invention, including the hardware implementation shown in FIG. 8, utilize a process performed in a feedforward manner at the output of the front-end. This avoids injecting noise at the input of the front-end, and does not limit the filter's attenuation.

Implementation of ASAR Processes

As shown in FIG. 8, the filtering performed by an ASAR system in accordance with some embodiments of this invention is performed in two phases: Phase I (Statistics Calculation Phase) and Phase II (Template Detection and Filtering Phase). A diagram explaining the statistic calculations performed in Phase I in accordance with some embodiments of the invention is shown in FIG. 9 and a diagram of template detection and adaptive filtering performed in Phase II in accordance with an embodiment of the invention is shown in FIG. 10.

Figure 9:
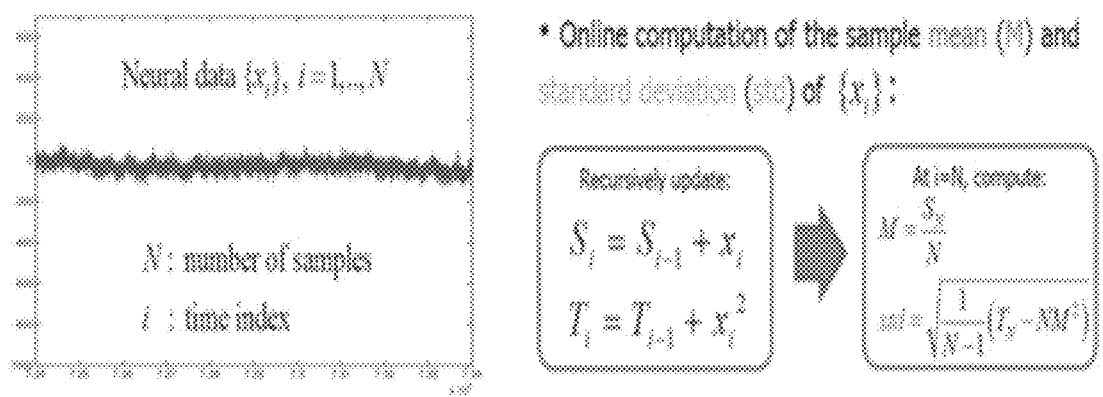
FIG. 9 illustrates calculation of statistics for the received neural signal in an absence of stimulation artifacts in accordance with an embodiment of the invention.
Figure 10:
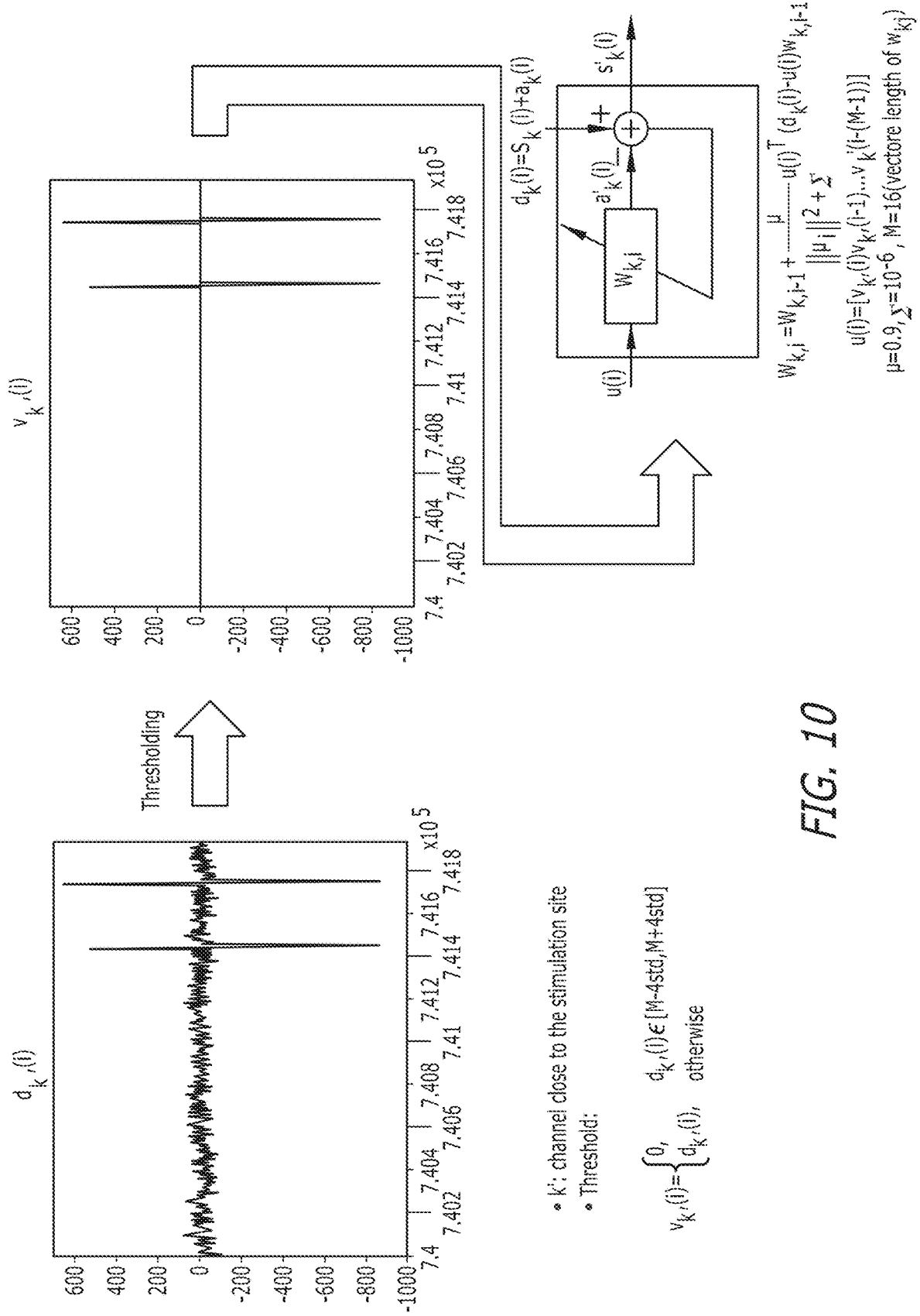
FIG. 10 illustrates a template detection and adaptive filtering technique for cancelling artifacts of simulation signals from received neural signals in accordance with an embodiment of the invention.

As shown in FIG. 9, statistics of a neural signal (average and standard deviation) can be calculated in the absence of any stimulation artifact. Based on these statistics, a threshold value can be set to detect artifacts, and a detection mode (phase II) activated. During phase II operation, a template is estimated from nearby recording channels when a stimulation artifact is present based on the threshold obtained from a previous phase. The template is applied to the adaptive filter to remove the artifact from the desired recording channel. The process of Phase II, with example values, is shown in FIG. 10.

Statistic Calculations

In accordance with some embodiments of the invention, the statistics for a neural signal are calculated in the following manner. The neural signal of an adjacent recording channel is sampled. Statistics of the neural signal from an adjacent recording channel are calculated in the absence of artifacts during the first N samples of the signal. and an appropriate threshold value is set. In accordance with many embodiments, the statistics are calculated by recursively updating the values $S_{(i)}=S_{(i-1)}+x_{(i)}$ and $T_{(i)}=T_{(i-1)}+x^2_{(i)}$, where $x_{(i)}$ is the input sample at time i. Mean (avg) and standard deviation (std) at time i=N are then calculated as (for N large enough):

$$avg = \frac{S(N)}{N}$$

$$std \approx \sqrt{\frac{1}{N-1}(T(N) - N\ avg^2)}$$

The number of samples N can be chosen as $N=2^n$ for some n in order to reduce the computational complexity of multiply/divide operations into simple binary shift operations, resulting in a more efficient hardware implementation in accordance with a number of embodiments.

Template Detection and Filtering

Figure 15:
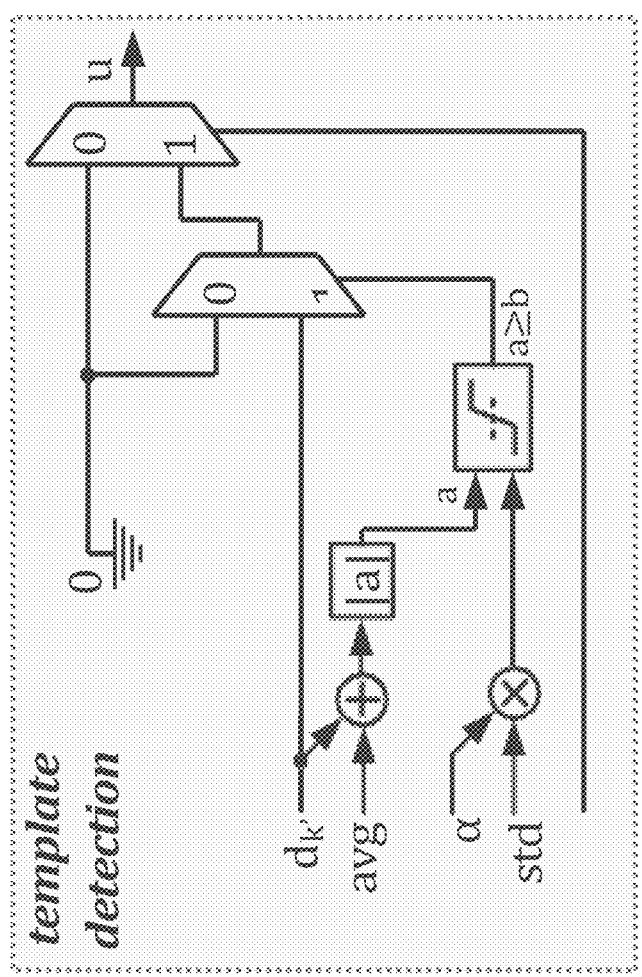
FIG. 15 illustrates components that perform a template detection process in accordance with an embodiment of the invention.

Components that perform a template detection process in accordance with an embodiment of the invention are shown in FIG. 15. Template detection in accordance with some embodiments of the invention is performed in the following manner. To clean the measurement $d_k(i)$ at an electrode, k, a nearby electrode, k', is selected. A template $u_i \in R^{1 \times 16}$ is determined. Based on the threshold obtained in the previous phase, $u_i(\ell)$, the $\ell$-th element of $u_i$ is estimated from $d_{k'}(i)$ through blanking within $\alpha \cdot std$ of the mean:

$$u_i = \begin{cases} d_{k'}(i-\ell), & \text{if } |d_{k'}(i-\ell) - avg| \geq \alpha \cdot std, \\ 0, & \text{otherwise} \end{cases}$$

Figure 16:
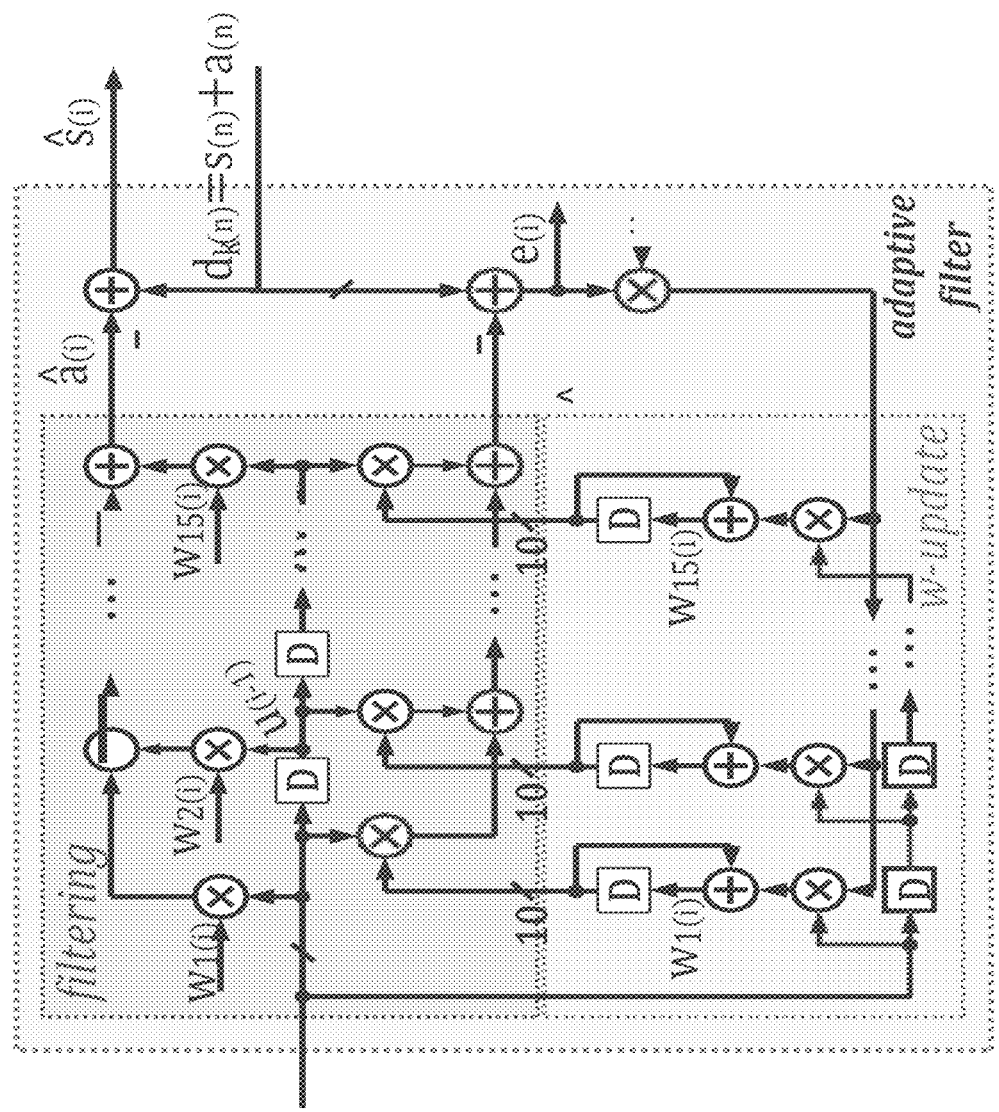
FIG. 16 illustrates an adaptive filter implemented in accordance with an embodiment of the invention.

The template is applied to a Normalized Least Mean Square (NLMS) 16-tap adaptive filter such as a filter described in A. H. Sayed, "Adaptive Filters", John Wiley & Sons, N J, 2008. A NLMS 16-tap adaptive filter in accordance with an embodiment of the invention is shown in FIG. 16. The clean neural signal, $\hat{s}_k(i)$, is then obtained by subtracting the estimated artifact $u_i w_{k,i}$ from $d_k(i)$ as follows:

$$w_{k,i} = w_{k,i-1} + \frac{\mu}{\|u_i\|^2 + \epsilon} u_i^T [d_k(i) - u_i w_{k,i-1}]$$

$$\hat{s}_k(i) = d_k(i) - u_i w_{k,i}$$

The filter in accordance with some embodiments has a latency of 16 sampling clock cycles, and operates in real-time. Additionally, the ASAR process can be implemented in a fully digital feed-forward manner that avoids injecting noise at the input of the front-end and does not limit the attenuation of the filter as no feedback DAC is required. Due to the feed-forward nature of ASAR, the error signal cannot be used directly as the estimate. As shown in the above equations, $\hat{s}_k(i)$ is to be obtained using the most recent coefficients, $w_{k,i}$.

Most current adaptive filter implementations use a classical Least Mean Squares algorithm, whereas ASARs in accordance with many embodiments of the invention use a normalized Least Means Square (LMS) variant. The LMS variant computes a variable step size at every iteration, as can be seen from the above equations, and requires 16 additional adders and multipliers but results in faster convergence times. An LMS adaptive filter in accordance with an embodiment of the invention is shown in FIG. 16.

In an ASAR process in accordance with some embodiments of the invention, the choice of the template $u_i$ is important. The stimulation pulse, as employed in some of prior arts approaches described above, is not suitable for this purpose because: (a) the mapping from stimulator through stimulation electrode, brain tissue and sensing electrode is highly non-linear, resulting in the need for complex filters and long convergence times, and (b) prior knowledge about the structural and temporal shape of the stimulation pulse is required. To remedy both drawbacks, a blind template detection method as described above may be implemented in accordance with many embodiments. A blind template detection method operates without information about the stimulation waveform. By obtaining a template from an adjacent electrode and learning only the mapping between adjacent recordings, a linear NLMS filter with 16 taps is sufficient. The use of a blind template detection method also enables an ASAR in accordance with a number of embodiments to work with any arbitrary stimulation pulse. Although the shown embodiment uses a linear NLMS filter with 16 taps, various other systems in accordance with various other embodiments may use other types of filters to meet the particular requirements of the particular systems.

Comparison of Results

Figure 11:
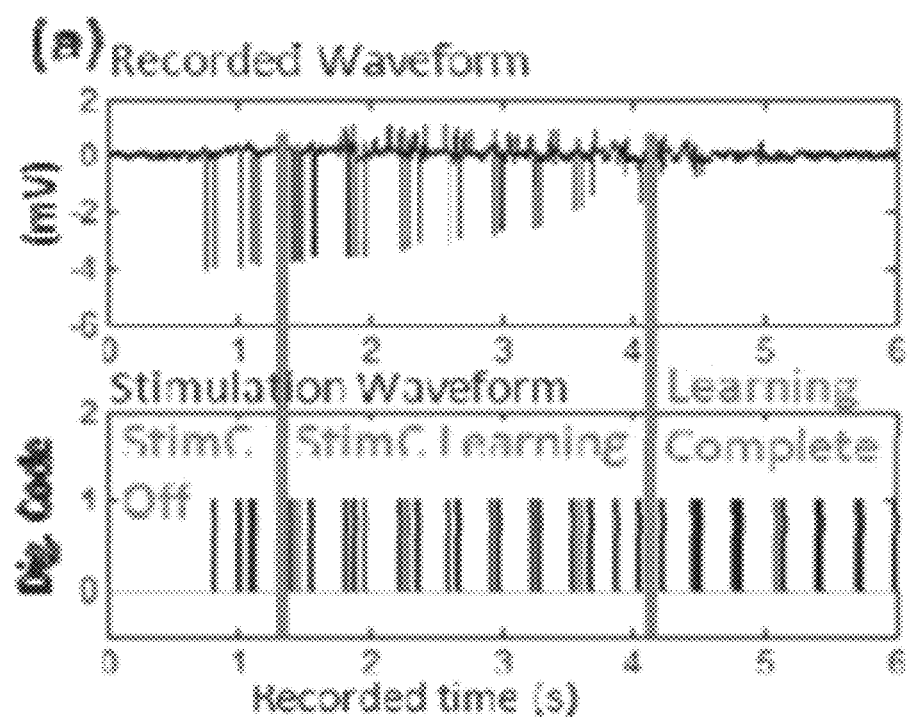
FIG. 11 illustrates waveforms generated by a bi-directional interface circuit with stimulation artifact cancellation and cross-channel common-mode noise suppression in accordance with an embodiment of the invention.

The results from a bi-directional interface circuit with stimulation artifact cancellation and cross-channel CM noise suppression are illustrated in FIG. 11. From FIG. 10, it is obvious that the artifact in the recorded waveform has an amplitude of ~4 mV, the convergence time is ~3 seconds, and this is a mono-phasic stimulation.

Figure 12:
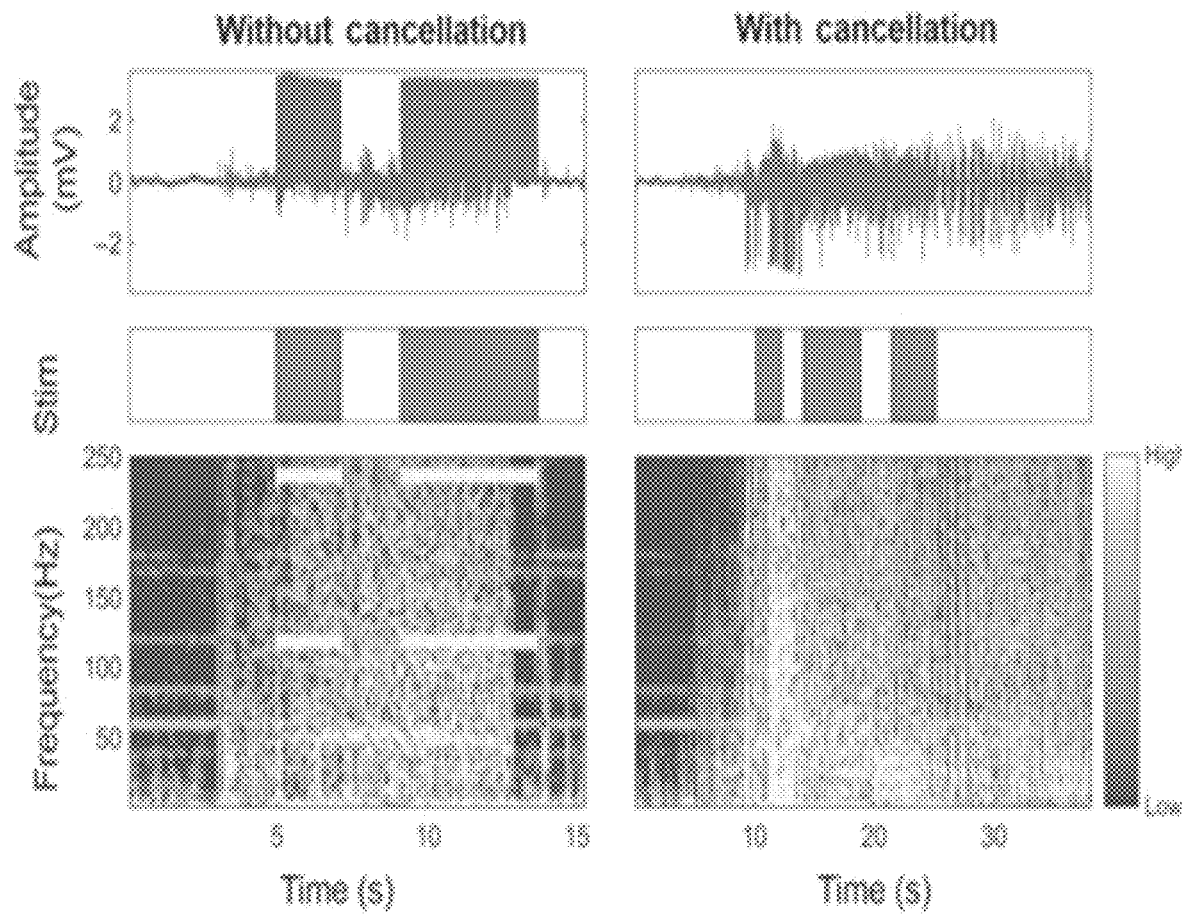
FIG. 12 illustrates waveforms generated by a bi-directional neural interface circuit with active stimulation artifact cancellation and cross-channel common-mode noise suppression in accordance with an embodiment of the invention.

The results of a bi-directional neural interface circuit with active stimulation artifact cancellation and cross-channel common-mode noise suppression are shown in FIG. 12. From FIG. 12, it is evident that the artifact in the recorded waveform has an amplitude of ~4 mV, and spectrogram of the time domain signals are shown in the bottom row.

Figure 13:
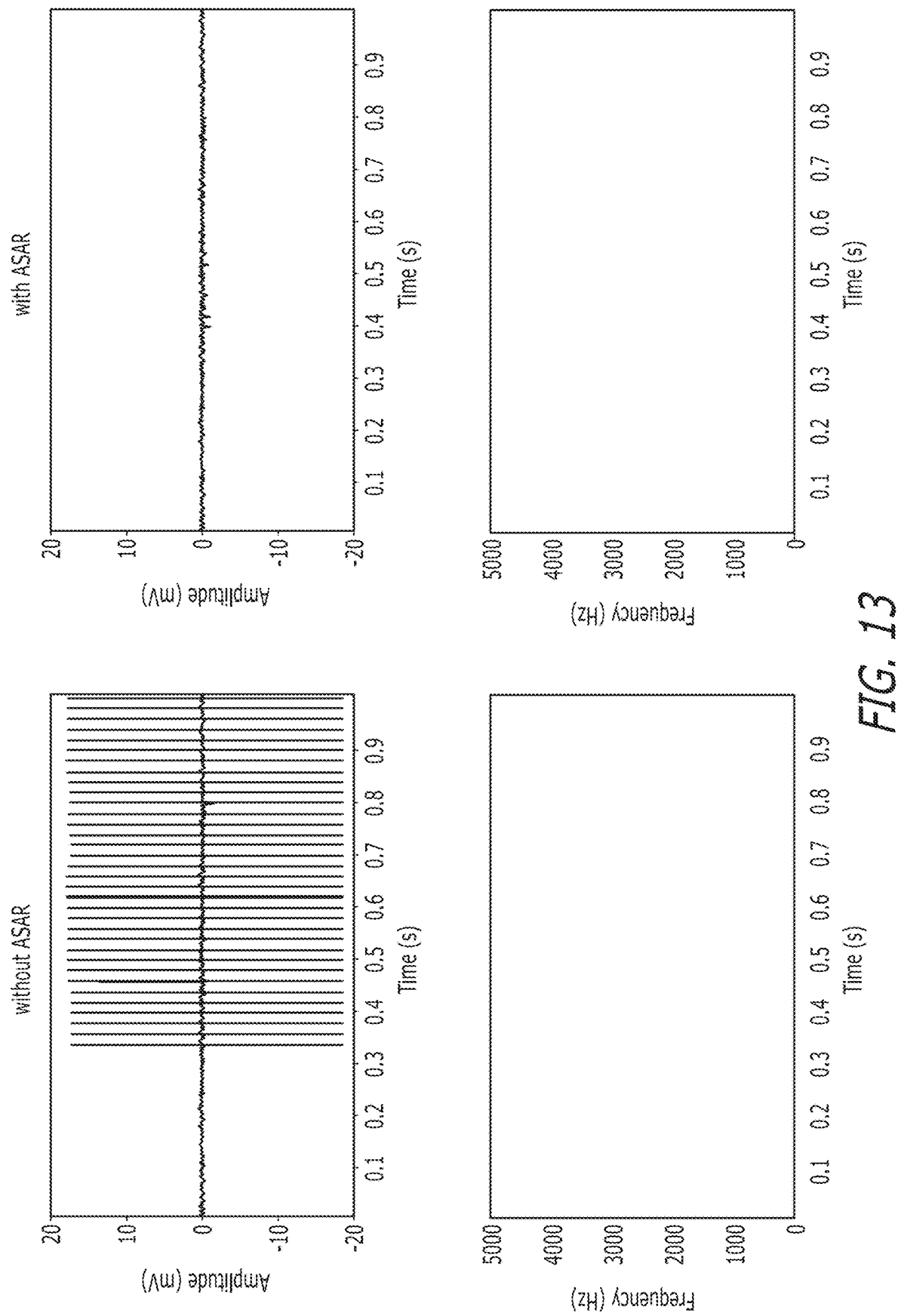
FIG. 13 illustrates raw time domain recorded neural signals and their spectrograms in accordance with an embodiment of the invention.
Figure 14:
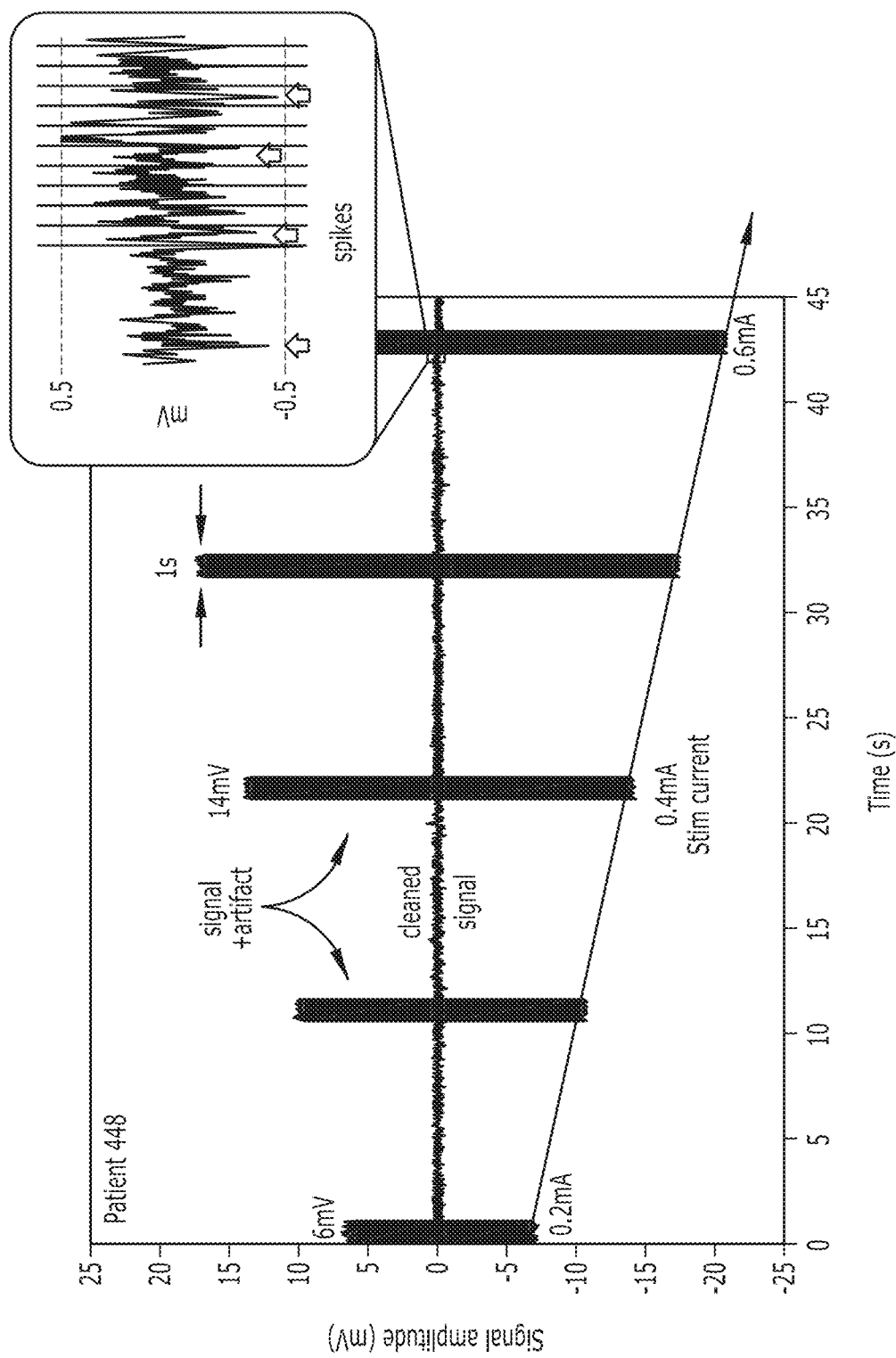
FIG. 14 illustrates a chart showing ASAR performance with varying stimulation levels in accordance with an embodiment of the invention.

The raw time-domain recorded neural signals with and without the use of an ASAR system in accordance with an embodiment of the invention are shown in FIG. 13 and the performance of an ASAR system in accordance with an embodiment of this invention with varying levels of stimulation signals is shown in FIG. 14. Based on the illustrated results, the convergence time for an ASAR system in accordance with an embodiment of the invention is more than 3000 times better than conventional state-of-the-art systems. This enables use with any arbitrary stimulation, and provides a practical solution to realize simultaneous stimulation and recording in neuro-modulation devices.

Although the present invention has been described in certain specific aspects, many additional modifications and variations would be apparent to those skilled in the art. It is therefore to be understood that the present invention may be practiced otherwise than specifically described, including various changes in the implementation, without departing from the scope and spirit of the present invention. Thus, embodiments of the present invention should be considered in all respects as illustrative and not restrictive.

What is claimed is:

1. A method for cancelling artifacts of stimulation signals from neural signals received by a neuro-modulation device comprising:

receiving neural signals from a plurality of sensors including a first sensor located adjacent to a second sensor;

receiving neural signals from the first sensor at a processing system wherein the received neural signals are in absence of stimulation artifacts;

determining statistics for neural signals received from the first sensor from the received neural signals using the processing system;

setting a threshold value for neural signals using the processing system based on the statistics for neural signals received from the first sensor;

determining, using a blind template detection process, a template for a stimulation artifact in a neural signal received at the second sensor by applying the threshold value to a signal simultaneously received at the first sensor using the processing system;

configuring an adaptive filter using the processing system based upon the template; and obtaining a clean neural signal from the neural signal received at the second sensor using the adaptive filter configured based upon the template.

2. The method of claim 1, wherein receiving neural signals from the first sensor includes sampling the neural signal from the first sensor to obtain a first N sample of the neural signal.

3. The method of claim 2, wherein N is chosen as $N=2^n$ for an n and the processing system performs multiply and divide operations using binary shift operations.

4. The method of claim 2, wherein the determined statistics for neural signals received from the first sensor include a mean of the neural signals and a standard deviation of the neural signals.

5. The method of claim 4 wherein statistics for neural signals received from the first sensor include:

recursively updating the values $S_{(i)}=S_{(i-1)}+x_{(i)}$ and $T_{(i)}=T_{(i-1)}+x^2_{(i)}$, where $x_{(i)}$ is the sample of the neural at time i, $S_{(i)}$ is the statistics at time i and $T_{(i)}$ is the threshold at time i;

determining a mean for the neural signals based on the following expression:

$$avg = \frac{S(N)}{N};$$

and determining the standard deviation of the neural signal based on the following expression:

$$std \approx \sqrt{\frac{1}{N-1}(T(N) - N\ avg^2)}.$$

6. The method of claim 5 wherein the template is represented as $u_i \epsilon R^{1 \times 16}$ and the determining of the template includes determining $u_i(\ell)$, the $\ell$-th element of the template, $u_i$, from the measurement of the neural signal at time i, $d_{k'}(i)$, based on the following:

$$u_i = \begin{cases} d_{k'}(i-\ell), & \text{if } |d_{k'}(i-\ell) - avg| \geq \alpha \cdot std, \\ 0, & \text{otherwise} \end{cases}$$

wherein $d_k(i)$ is a measurement at an electrode, k, and k' is a nearby electrode.

7. The method of claim 6 wherein a clean neural signal, $\hat{s}_k(i)$, is obtained by subtracting the estimated artifact $u_i w_{k,i}$ from $d_k(i)$ as follows:

$$w_{k,i} = w_{k,i-1} + \frac{\mu}{\|u_i\|^2 + \epsilon} u_i^T [d_k(i) - u_i w_{k,i-1}]$$

$$\hat{s}_k(i) = d_k(i) - u_i w_{k,i}$$

where $w_{k,i}$ is a filter coefficient and $\hat{s}_k(i)$ is the clean neural signal.

8. The method of claim 1, wherein the adaptive filter is a Normalized Least Mean Square (NLMS) adaptive filter.

9. The method of claim 8, wherein the NLMS adaptive filter is a 16-tap NLMS adaptive filter.

10. A system for cancelling artifacts of stimulation signals from neural signals received by a neuro-modulation device comprising:

a processor; and memory readable by the processor that stores instructions that when read by the processor direct the processor to:

receiving neural signals from a plurality of sensors including a first sensor located adjacent to a second sensor;

receive neural signals from the first sensor, wherein the received neural signals are in absence of stimulation artifacts;

determine statistics for neural signals received from the first sensor from the received neural signals;

set a threshold value for neural signals based on the statistics for neural signals received from the first sensor;

determine, using a blind template detection process, a template for a stimulation artifact in a neural signal received at the second sensor by applying the threshold value to a signal simultaneously received at the first sensor;

configure an adaptive filter based upon the template; and obtaining a clean neural signal from the neural signal received at the second sensor using the adaptive filter configured based upon the template.

11. The system of claim 10 wherein receiving neural signals includes sampling the neural signal from the first sensor to obtain a first N sample of the neural signal.

12. The system of claim 11 wherein N is chosen as $N=2^n$ for an n and the instructions read by the processor execute multiply and divide operations using binary shift operations.

13. The system of claim 11 wherein the determined statistics for neural signals received from the first sensor include a mean of the neural signals and a standard deviation of the neural signals.

14. The system of claim 13 wherein the instructions to determine statistics for neural signals received from the first sensor include instructions that direct the processor to:

recursively update the values $S_{(i)}=S_{(i-1)}+x_{(i)}$ and $T_{(i)}=T_{(i-1)}+x^2_{(i)}$, where $x_{(i)}$ is the sample of the neural at time i, $S_{(i)}$ is the statistics at time i and $T_{(i)}$ is the threshold at time i;

determine the mean for the neural signals based on the following expression:

$$avg = \frac{S(N)}{N};$$

and
   determine the standard deviation of the neural signal based on the following expression:

$$std \approx \sqrt{\frac{1}{N-1}(T(N) - N\ avg^2)}.$$

15. The system of claim 14 wherein the template is represented as $u_t \in R^{1 \times 16}$ and the determining of the template includes determining $u_t(\ell)$, the $\ell$-th element of the template, $u_t$, from the measurement of the neural signal at time i, $d_{k'}(i)$, based on the following:

$$u_i = \begin{cases} d_k, (i - \ell), & \text{if } |d_k, (i - \ell) - avg| \geq \alpha \cdot std, \\ 0, & \text{otherwise} \end{cases}.$$

wherein $d_k(i)$ is a measurement at an electrode, k, and k' is a nearby electrode.

16. The system of claim 15 wherein a clean neural signal, $\hat{s}_k(i)$, is obtained by subtracting the estimated artifact $u_i w_{k,i}$ from $d_k(i)$ as follows:

$$w_{k,i} = w_{k,i-1} + \frac{\mu}{\|u_i\|^2 + \epsilon} u_i^T [d_k(i) - u_i w_{k,i-1}]$$

$$\hat{s}_k(i) = d_k(i) - u_i w_{k,i}$$

where $w_{k,i}$ is a filter coefficient and $\hat{s}_k(i)$ is the clean neural signal.

17. The system of claim 10 wherein the adaptive filter is a Normalized Least Mean Square (NLMS) adaptive filter.

18. The system of claim 17 wherein the NLMS adaptive filter is a 16-tap NLMS adaptive filter.

19. A system for cancelling artifacts of stimulation signals from neural signals received by a neuro-modulation device comprising:
   circuitry configured to receive neural signals from a plurality of sensors including a first sensor located adjacent to a second sensor;
   circuitry configured to receive neural signals from the first sensor, wherein the received neural signals are in absence of stimulation artifacts;
   circuitry configured to determine statistics for neural signals received from the first sensor from the received neural signals;
   circuitry configured to set a threshold value for neural signals based on the statistics for neural signals received from the first sensor;
   circuitry configured to determine, using a blind template detection process, a template for a stimulation artifact in a neural signal received at the second sensor by applying the threshold value to a signal simultaneously received at the first sensor;
   circuitry configured to configure an adaptive filter based upon the template;
   circuitry configured to receive neural signals from the second sensor; and
   circuitry configured to remove stimulation artifacts from the neural signals from the second sensor using the adaptive filter to obtain clean neural signals.

* * * * *